US012599288B2

(12) United States Patent
Joshi et al.

(10) Patent No.: US 12,599,288 B2
(45) Date of Patent: Apr. 14, 2026

(54) ENDOSCOPIC CAMERA ARRANGEMENT AND METHOD FOR CAMERA ALIGNMENT ERROR CORRECTION

(71) Applicant: Erbe Vision GmbH, Wurmlingen (DE)

(72) Inventors: Shirish Joshi, Wurmlingen (DE); Faisal Kalim, Reutlingen (DE); Subhamoy Mandal, Kolkata (IN)

(73) Assignee: Erbe Vision GmbH, Wurmlingen (DE)

( * ) Notice: Subject to any disclaimer, the term of this patent is extended or adjusted under 35 U.S.C. 154(b) by 593 days.

(21) Appl. No.: 17/971,114

(22) Filed: Oct. 21, 2022

(65) Prior Publication Data

US 2023/0125959 A1 Apr. 27, 2023

(30) Foreign Application Priority Data

Oct. 25, 2021 (EP) ..................................... 21204573

(51) Int. Cl.
*A61B 1/00* (2006.01)
*G02B 23/24* (2006.01)

(52) U.S. Cl.
CPC ...... *A61B 1/00096* (2013.01); *A61B 1/00163* (2013.01); *G02B 23/2407* (2013.01)

(58) Field of Classification Search
CPC ............ A61B 1/00057; A61B 1/00096; A61B 1/00172; A61B 1/00183; A61B 2090/3937; A61B 2034/2055; A61B 2034/2057; A61B 2034/2072; A61B 2090/0811; A61B 2090/0812; A61B 2090/363; A61B 2090/364; A61B 2090/365; A61B 2090/366; A61B 2090/367; A61B 2090/368; A61B 2090/3941;

(Continued)

(56) References Cited

U.S. PATENT DOCUMENTS 4,558,691 A * 12/1985 Okada ................... A61B 5/1076
600/117
2003/0114730 A1 6/2003 Hale et al.
(Continued)

FOREIGN PATENT DOCUMENTS

DE 10 2008 057 734 B4 7/2016
DE 10 2018 121 711 A1 3/2020
(Continued)

*Primary Examiner* — Michael J Carey
*Assistant Examiner* — Stephen Floyd London
(74) *Attorney, Agent, or Firm* — Blank Rome LLP

(57) ABSTRACT

Augmented reality applications require precise camera calibration to reduce the overall target registration errors. The camera calibration determines the mathematical model of the camera in order to determine how the physical world space is mapped to the camera image space and thus is highly dependent on the optics of the camera. The camera calibration algorithm normally assumes that the optics of the camera is rigidly fixed, which in fact is not at least for tilted laparoscopic cameras as illustrated in FIGS. 6 to 8. Furthermore, any mechanical play between elements of the objective and the image converter will render the optics variable. According to the invention markers to will be placed within the field of view of the laparoscopic camera, which allows for determination of rotation of the optical part and mechanical misalignment without the necessity or providing any additional sensor.

13 Claims, 5 Drawing Sheets

(58) Field of Classification Search
CPC ...... A61B 2090/3945; A61B 2090/395; G02B 27/32; G02B 27/34; G02B 27/36
See application file for complete search history.

(56) References Cited

U.S. PATENT DOCUMENTS

| | | | |
|---|---|---|---|
| 2005/0027167 A1 | 2/2005 | Chatenever et al. | |
| 2005/0159646 A1* | 7/2005 | Nordstrom | A61B 1/00062 |
| | | | 600/476 |
| 2009/0062658 A1* | 3/2009 | Dunki-Jacobs | A61B 5/0084 |
| | | | 600/478 |
| 2014/0303491 A1 | 10/2014 | Shekhar et al. | |
| 2015/0012081 A1 | 1/2015 | Robin | |
| 2016/0191901 A1 | 6/2016 | Stegall et al. | |
| 2016/0338574 A1* | 11/2016 | Fujimori | G02B 23/02 |
| 2018/0279868 A1* | 10/2018 | Sczaniecka | A61B 8/445 |
| 2019/0328216 A1 | 10/2019 | Beyer et al. | |
| 2019/0335104 A1* | 10/2019 | Sugie | A61B 1/00096 |
| 2020/0187766 A1* | 6/2020 | Zalevsky | A61B 1/00186 |
| 2021/0278645 A1* | 9/2021 | Banerjee | G02B 23/243 |
| 2022/0151475 A1* | 5/2022 | Hallen | A61B 1/00045 |
| 2022/0180096 A1* | 6/2022 | Hinding | G06K 7/1417 |

FOREIGN PATENT DOCUMENTS

| | | | |
|---|---|---|---|
| EP | 1 692 996 A2 | 8/2006 | |
| EP | 2 429 376 A2 | 3/2012 | |
| EP | 3 539 457 A1 | 9/2019 | |
| JP | 2004147777 A | 5/2004 | |
| JP | 2010-8483 A | 1/2010 | |
| JP | 2015518391 A | 7/2015 | |
| JP | 2022000141 A | 1/2022 | |
| WO | WO 2010/129324 A2 | 11/2010 | |
| WO | WO 2020/219709 A1 | 10/2020 | |
| WO | 2021171465 A1 | 9/2021 | |

* cited by examiner

ENDOSCOPIC CAMERA ARRANGEMENT AND METHOD FOR CAMERA ALIGNMENT ERROR CORRECTION

CROSS-REFERENCE TO RELATED APPLICATION

This application claims priority to European Application No. 21204573.6, filed Oct. 25, 2021, the entirety of which is incorporated by reference herein.

TECHNICAL FIELD

Embodiments of the invention described herein relate to an endoscopic, in particular laparoscopic camera arrangements. Embodiments of the invention also relate to a method for correcting calibration of an image captured by laparoscopic camera arrangements.

BACKGROUND

Laparoscopic cameras typically have a stiff elongated shaft adapted to be placed within a patient's body for capturing live images during surgery typically performed with laparoscopic instruments. The laparoscopic camera produces images the surgeon can view during surgery for performing and controlling surgery.

German patent application DE 10 2018 121 711 A1 discloses an endoscopic camera having an elongated shaft with an optical system placed at the distal end thereof. The optical system involves an objective and an electronic image converter.

A sideward looking endoscopic camera can be taken from US patent publication no. US 2015/012081 A1. On the distal end of the shaft of the video endoscope an objective is provided which is movable relative to an image sensor about the longitudinal axis of the shaft. The viewing direction may be changed over from a first viewing direction to a second viewing direction on account of a viewing direction change-over command.

Japanese patent publication JP 2010008483 A discloses an imaging device capable of displaying position information and/or azimuth information when performing remote visual inspection of an object to be inspected, e.g. a long tubular structure. An acceleration sensor and/or a terrestrial magnetism sensor are arranged at an imaging part. The position and azimuth information output from the sensors is combined with a video signal from the imaging part.

Furthermore, US Patent publication US 2005/027167 A1 discloses an apparatus for compensating the display of an image obtained from a video camera system of an endoscope as it is moved through various orientations. The received optical image is converted to an electrical signal with an image sensor. The endoscope video camera system comprises an inertial sensor to sense rotations of the received image about the optical axis of the endoscope. The sensor's output signals are used to rotate either the image or the image sensor. In case of rotation of the image sensor the rotation sensor can be a gyroscope or a pair of accelerometers.

An interface for a variable direction of view endoscope can be taken from US 2003/114730 A1. The interface has an input device for receiving commands from the user, an output device for adjusting the endoscope, and an electronic processing device to determine the appropriate output based on the given input. The processing device may be configured to allow operation assisting features including a coordinate system aligned with the current view, a coordinate system aligned with the user's surroundings, a coordinate system aligned with the operating cavity, a memory to facilitate the immediate return to a user selected direction of view, and a clear indication of the current direction of view.

Further prior art can be taken from EP 1 692 996 A2, EP 2 429 376 A2, DE 10 2008 057 734 B4, EP 3 539 457 A1.

SUMMARY

During surgery external forces may act on the elongated shaft and the optical system and lead to image dislocations in the image sensor. Those dislocations may have detrimental effects on the accuracy on the operation results. Therefore, it is an objective of the present invention to avoid the detrimental effects of those dislocations.

The inventive concept provides an endoscopic, in particular a laparoscopic camera arrangement comprising an elongated shaft extending along a centre axis from a proximal end to a distal end and adapted for being introduced into an animal's or human's body. The shaft comprises a light entry window at the distal end thereof and a camera placed in or at the proximal end of the shaft or at the distal end, alternatively. The camera comprises an image converter and an objective optically coupled to the image converter. The image converter may be a camera chip adapted to convert an optical image projected onto the surface of the chip into electric image signals. According to the invention at least one optical marker is placed within the optical path of the objective for being projected onto the image converter.

The inventive concept allows for detection and correction of deformations, misplacements and movements the objective may undergo relative to the image converter during surgery, no matter whether caused inadvertently or intentionally. Those movements, deformations or misplacements will relocate the image of the at least one optical marker at the image converter. So a mathematical projection model of the laparoscopic camera arrangement may be corrected according to the change of the position of the objective relative to the image converter. The change of the position of the objective may in particular be a rotation of the objective or parts thereof around the longitudinal axis of the shaft as is the case with obliquely or sideways looking objectives. The mechanical deformation or dislocation of the objective will be derived from the relocation of the images of the markers projected onto the image converter and used for correcting the position data of all images captured by the camera arrangement. The position data indicate the spatial location of the object imaged by the laparoscopic camera.

The at least one optical marker may be placed in an image plane of the objective or at the light entry window of the optical system placed at the distal end of the shaft. Preferably, the optical system defines a depth definition such that the at least one optical marker is placed therein.

In certain embodiments the objective is rotationally fastened to the image converter whereas in preferred embodiments the objective or parts thereof may be movably connected to the image converter. In particular, the objective may comprise an adapter with the light entry window provided thereon and rotatably fastened relative to the image converter. This is in particular useful if the objective is a "sideward looking" objective the optical axis of which is inclined relative to the longitudinal axis of the shaft. By rotating the distal part of the objective or the complete objective the viewing direction may change. The inventive concept allows for determining the rotational position of the viewing direction without any additional sensor.

The inventive camera arrangement preferably comprises at least one, preferably two, three four or more optical markers placed within the optical path within the field of sight. Preferably, any of the optical markers comprises a unique pattern so that all optical markers together form an asymmetric structure. So the markers cannot be confused no matter how far the objective or parts thereof are rotated. The markers can, and preferably will, be placed in mirror symmetry one to another though without themselves being symmetric one to another. Preferably, the optical markers remain within the field of sight during changes of the position of the objective, such as rotations of the objective or parts thereof around the longitudinal axis of the shaft as is the case with obliquely or sideways looking objectives.

The invention is in particular useful in connection with augmented reality applications and some other applications, which typically require precise camera calibration in order to reduce the overall target registration errors or in order to get the accurate position of structures from laparoscopic image. For camera calibration, regularly, numerous images of a known calibration grid have to be taken from multiple poses and then fed to the camera calibration algorithms. The camera calibration basically tries to determine the mathematical model of the camera in order to determine how the physical world space is mapped to the camera image sensor space. The mathematical model of the camera is highly dependent on the optics of the camera. Normally, the camera calibration algorithm makes the assumption that the optics of the camera is rigidly fixed. However, since this is not the case for tilted rotatable laparoscopic cameras, the invention provides an easy way for camera calibration. This is also true if bending forces act on the somewhat flexible shaft of the laparoscope.

An optical coupler may be used to connect the camera unit with the camera sensor to the laparoscope. The coupler will rotatably connect the shaft of the laparoscope to the camera unit. Rotating the shaft will be necessary in particular with obliquely or sideward looking optics at the distal end of the shaft. Inevitably present mechanical play at the coupler may lead to uncertainties how the physical world space is mapped to the image converter of the camera. Those uncertainties and/or rotation of the optics of the laparoscope may be tracked by the optical markers so that the mathematical model of the camera may be adapted or corrected.

The laparoscope may comprise triangulation marks or bodies (e.g. a position indicator including a set of triangulation marks or bodies) firmly connected to the proximal end of the laparoscope for detecting the position and orientation of the laparoscope.

Any flexible deformation of the shaft will shift the image on the camera sensor and so decrease the accuracy of the localisation of the image. The optical markers will help to detect those localization errors and to correct them. Preferably the optical markers are placed at or in the vicinity of the light entry window or at least close to the distal end of the shaft. So it will become possible to reliably detecting localization errors caused by shaft deflection. In any case the optical markers will be placed such that any parts of the laparoscope which may cause a dislocation of the image on the sensor will be placed between the markers and the image sensor. Those parts may be the flexible shaft and the coupler.

BRIEF DESCRIPTION OF THE DRAWINGS

Further details of the embodiments of the inventive camera arrangement can be taken from the description, claims and the drawing in which:

DETAILED DESCRIPTION

Figure 1:
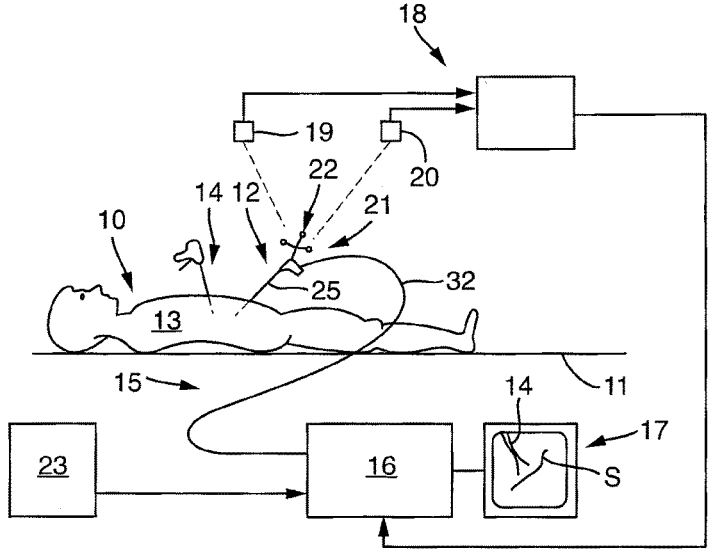
FIG. 1 illustrates a camera arrangement and a patient during surgery.

FIG. 1 illustrates an operation site with a patient 10 lying on a patient support table 11 with a laparoscopic camera 12 placed within the body 13 of the patient 10 during laparoscopic surgery. A laparoscopic instrument 14 may also be placed within the patient's body 13 for performing surgery. The laparoscopic camera 12 belongs to a laparoscopic camera arrangement 15, which involves the laparoscopic camera 12, a processing unit 16 and a display unit 17. The display unit 17 may be a screen for displaying live images taken up by the laparoscopic camera 12. It is also possible to use a virtual reality arrangement (VR) instead of a screen for presenting the live images of the laparoscopic camera 12 to the surgeon.

Figure 2A:
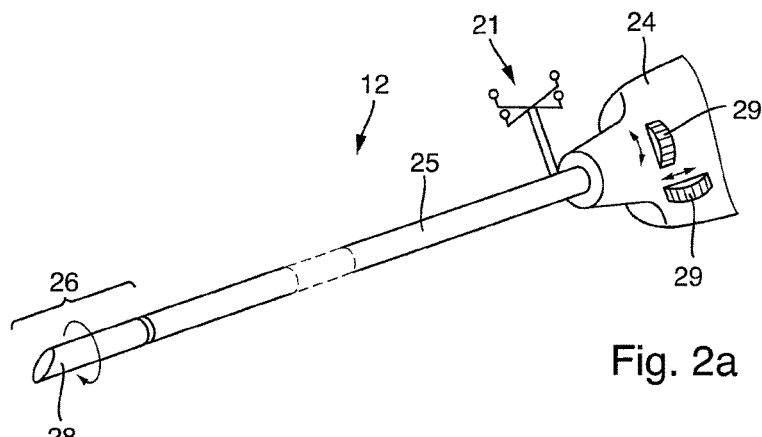
FIGS. 2a and 2b illustrate perspective views of laparoscopic camera arrangements.
Figure 2B:
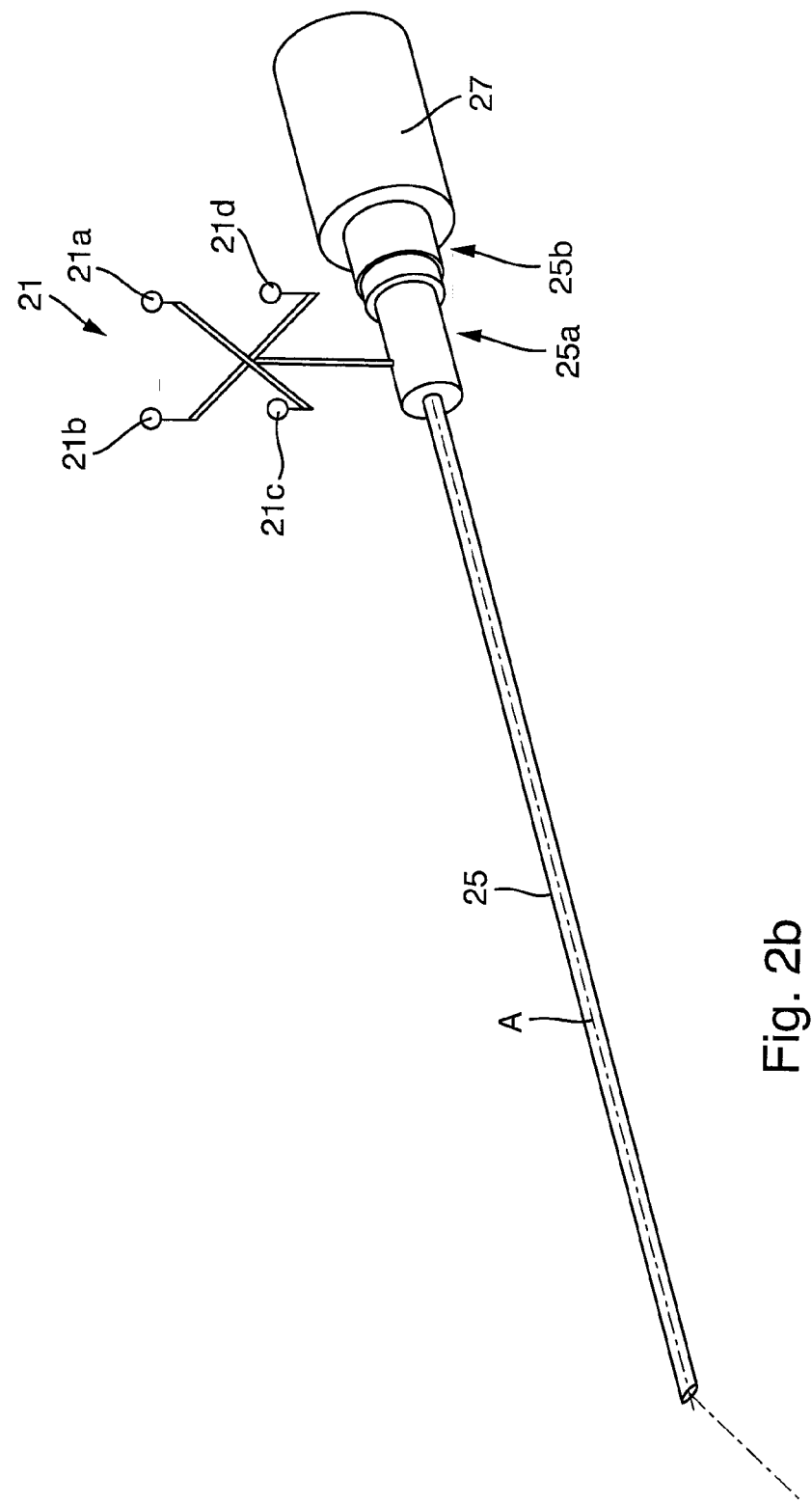

The laparoscopic camera 12 may be connected to a location system 18 adapted to locate the laparoscopic camera 12 relative to the position of the patient 10. The location system 18 may comprise two or more sensors 19, 20 for detecting the spatial position of the camera 12. As illustrated in FIGS. 2a and 2b, a position indicator 21 may be provided on the camera 12, which indicator 21 may be located within space by triangulation. The position indicator 21 may comprise a set 22 of indicator bodies or triangulation marks (bodies) 21a-21d for unambiguously detecting the location and the orientation of the shaft 25 of the camera 12. The position indicator 21 may be rigidly connected to the shaft 25, in particular to the proximal end 25a of the shaft 25. It is to be understood that any other type of position sensing means and methods can be used for determining position data of the laparoscopic camera 12.

The processing unit 16 may receive data from a medical imaging system 23, which data represent medical scan images of the region of the body 13 in which the surgery is performed. Alternatively, the data may represent graphical representations of crucial structures of interest like malignant tissue or a combination of a scan image and graphical representations. The processing unit 16 is adapted to overlay the medical image provided by the medical imaging system 23 and the live image supplied by the laparoscopic camera 12. The display unit 17 may reproduce the live image with the medical image or structures thereof registered with the live image. The processing unit 16 may additionally or alternatively be adapted to overlay the live image and a graphic representation derived from the medical image. The graphical representation may indicate specific tissue structures of interest.

For registering the live image and the scan image of the imaging system 23 (and/or the graphical representation) the precise position of the structure seen by the camera 12 must be known and available to the processing unit 16. Therefore, camera 12 has to be calibrated. For camera calibration numerous images of a known calibration grid may be taken for multiple purposes and then fed to camera calibration algorithms, which may run on processing unit 16. The camera calibration algorithms produce a mathematical model of the camera.

It turned out that the mathematical model taken during calibration outside the patient's body 13 may not be completely valid during surgery. This is in particular true, if forces acting on the objective cause some deformation or dislocation. Moreover, the mathematical model may need input characterizing the viewing direction of an obliquely viewing objective i.e. the turning position of a rotatable objective.

In another embodiment the inventive laparoscopic camera arrangement 15 may be used without registering the live image with data from any medical imaging system. The optical markers placed at the distal end, which markers are imaged at the image sensors, will indicate any mechanical inaccuracy caused by play or deflection of items between the markers and the image sensor. This will allow for correction of position data obtained measuring the position of the position indicator 21 e.g. by triangulation. If an image recognition algorithm is applied to the images for detecting physiologic structures, correcting imaging failures caused by mechanical play or deflection of the shaft will allow for precisely determining the true position of tissue structures detected.

FIG. 2a illustrates one embodiment of the laparoscopic camera 12 comprising a handle 24 fixed to a shaft 25 having a camera system 26 at the distal end thereof. The camera system 26 comprises a camera unit 27 as illustrated in FIG. 3 or FIGS. 6, 7 and 8. The camera system 26 may have a portion 28 rotatable mounted on the distal end of shaft 25. The rotation may be controlled by a thumb wheel 29 or any other element may be placed on handle 24. Another thumb wheel 30 may be provided on the handle 24 for moving a respective part of the camera system 26 in order to move the focus plane and/or for providing zoom function by moving one or more optical elements in longitudinal direction.

FIG. 2b illustrates another embodiment of the laparoscopic camera 12 comprising a handle 24 fixed to a shaft 25 having a camera system 26 at the distal end thereof. The camera system 26 comprises a camera unit 27 as illustrated in FIG. 3 or FIGS. 6, 7 and 8. The camera system 26 may have a portion 28 rotatable mounted on the distal end of shaft 25. The rotation may be controlled by a thumb wheel 29 or any other element may be placed on handle 24. Another thumb wheel 30 may be provided on the handle 24 for moving a respective part of the camera system 26 in order to move the focus plane and/or for providing zoom function by moving one or more optical elements in longitudinal direction.

The camera system 26 comprises an image converter 31, e.g. a semiconductor chip for transferring an image projected onto its surface into electrical signals fed to the processing unit 16 via a cable 32 or any other suitable transmission means.

The camera system 26 comprises an objective 33 comprising at least one, preferably two or more lenses 34, 35 for projecting an image of a real object 36 onto the surface of the image converter 31 of the camera unit 27. The objective 33 may comprise several lenses (34, 35), an aperture 37 and a light entry window 38 next to the object 36. Furthermore, the objective may comprise optical markers 39, 40, 41, 42 placed in a peripheral region of a carrier such that images of the markers 39 to 42 are projected on the image converter 31. The markers 39 to 34 may be placed on the light entry window 38 or at a separate carrier placed e.g. at the position of the real image plane 43, where a real image exists between the lenses 34, 35. If the markers 39 to 42 are placed on the light entry window 38 the light entry window 38 is preferably arranged in the area of depths of field of the objective 33. Preferably the markers 39, 40, 41, 42 are placed as far as possible away from the image sensor 31, e.g. at the distal end of the instrument 12.

Figures 3, 4, 5:
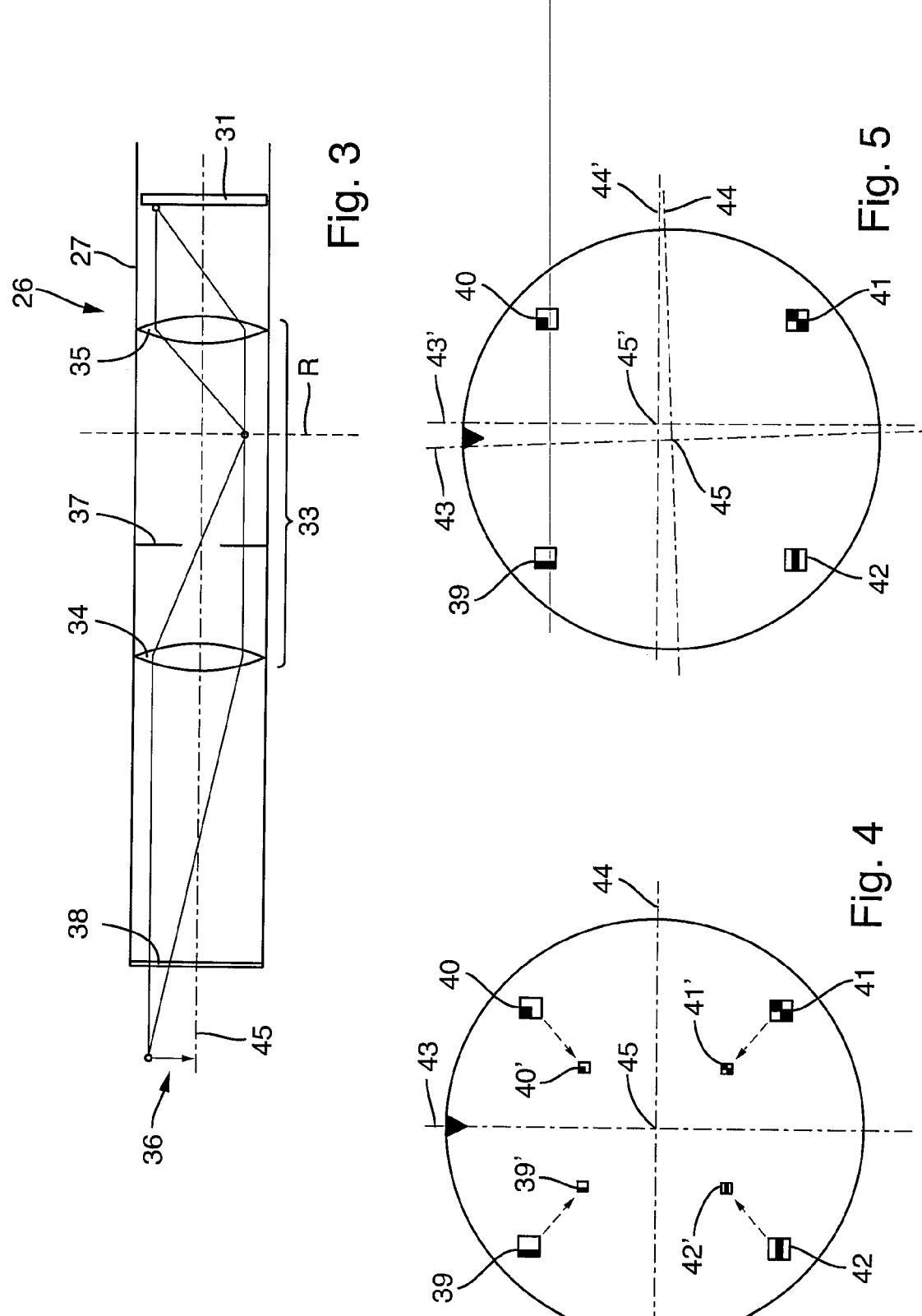
FIG. 3 illustrates a schematic longitudinal sectional view of the distal end of the laparoscopic camera arrangement according to FIG. 2a, FIG. 4 illustrates optical markers of the camera arrangement as seen by the image converter with no distortion, FIG. 5 the optical markers as seen by the image converter with the laparoscope subjected to mechanical inaccuracies, mechanical play and/or subjected to pending forces, FIG. 6 a schematic longitudinal sectional view of the distal end of the laparoscopic camera arrangement comprising a light entry window looking sideways, FIG. 7 a schematic partial illustration of an obliquely viewing objective, FIG. 8 a perspective illustration of the distal end of an obliquely viewing laparoscopic camera, and FIG. 9 the optical image converter with the objective rotated and distorted.
Figure 6:
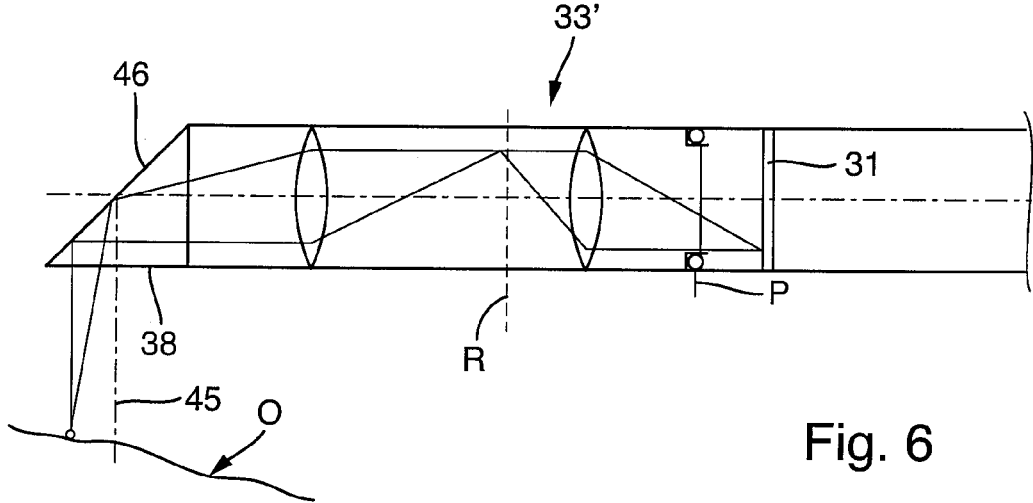

While according to FIG. 2a the camera system 26 is completely arranged on the distal end of the instrument 12, the camera system 26 may according to FIG. 2b comprise the objective 33 placed at the distal end of the shaft 25 (and/or along the shaft), whereas the camera unit 27 with the image converter 31 is located at the proximal end of the shaft. The objective 33 is optically connected to the image converter 31 by means of lenses arranged in the shaft. FIGS. 3 and 6 illustrate the objective 33 and the camera unit 27 by its basic principle which may work with the embodiment of FIG. 2a and with the embodiment of FIG. 2b as well. A swivel joint coupling 25b mechanically couples the camera unit 27 to the distal end 25a of the shaft.

The swivel joint coupling allows rotating the shaft 25 around its longitudinal axis A. Moreover the swivel joint coupling 25b detachably connects the camera unit 27 to the shaft 25. As is to be preferred for all embodiments of the invention, both, the swivel joint coupling 25b is located between the camera unit 27 and the markers 39, 40, 41, 42. In the embodiment of FIG. 2b both, the somewhat flexible shaft 25 and the swivel joint coupling 25b are located between the camera unit 27 and the markers 39, 40, 41, 42. So all relevant sources of inaccuracies are captured between the camera unit 27 and the markers 39, 40, 41, 42.

The inventive camera arrangement preferably uses four markers 39 to 42 while it is possible to use a different number of markers e.g. one, two, tree, five or more. Basically, any number of markers and any type of markers may work. However, it is highly preferred to use unique markers so that each marker 39, 40, 41, and 42 has an individual design, which is both, unique and indicative of its position. In other words, preferably no marker 39 through 34 is congruent to any other of the markers neither by shifting nor by rotating it.

As can be taken from FIG. 4, the markers 39 to 42 do not form a symmetric pattern. Due to the unique design of the markers 39 to 42 there is no symmetry neither in view of the vertical line 43 nor in view of the horizontal line 44 nor in view of the optical axis 45 shown in FIG. 4. Any marker 39-42 can be a unique QR-code or Aruco Marker. The places of the markers 39-42 however, may be located symmetrically to the lines 43 and 44, which cross each other at a right angle. In another embodiment the markers 39 to 42 are not placed symmetrically relative to the lines 43, 44. The markers 39-42 can be placed at the corners of a rectangle, a square, a rhombus or a trapeze. Other patterns are possible though.

The inventive system operates as follows:

During operation, the laparoscopic camera 12 will be located by the location system 18 and will take up live images, which are delivered to the processing unit 16 for reproduction on the display unit 17. Medical scan images supplied by medical imaging system 23 may be overlaid to the scan image so that the display unit 17 displays the live image of the tool of the instrument 14, live reproduction of the live tissue and one or more structures S, which may be taken from the medical scan image or may be graphical representations of tissue structures detected in the medical scan image.

It may be that the laparoscopic camera 12 undergoes some deformation of the shaft 25 or some misalignment of the image converter 31 relative to the objective 33 due to mechanical play, bending forces or due to other causes. If bending forces result in a displacement of the objective 33 the pattern of markers 39 to 42 will be displaced as illustrated in FIG. 5. The displacement of the markers 39 to 42 may form a basis for detecting and correcting the misalignment of the image converter 31 relative to the objective 33. A homography matrix may be calculated and used for recalculating the pictures acquired by the image converter. So the pictures will be correct with the distortions removed.

FIG. 5 illustrates the shift of the optical axis 45 in the centre of the image due to the misalignment of the image converter 31 relative to the objective 33 with a new optical axis 45' established. The processing unit 16 detects the displacement of the markers 39 to 42 and corrects the mathematical model of the camera 12. The corrected camera model will allow for correct registering the live image with the scan image so that the surgeon will not be misled by not correctly registered scan and live images.

While the camera system 26 according to FIG. 3 is axially oriented (i.e. looks parallel to the axial optical axis 45) for demonstration purposes and while the objective 33 may have a fixed focal length, it is possible to move one or two of the lenses for changing the focal length and/or for providing a zoom effect by turning thumb wheel 30. Both may change the positions of the markers 39 through 42 as is indicated in FIG. 4 by markers 39' through 42'. Again the processing unit 16 may revise the camera model according to the displacement of the projections of the markers 39' to 34' on image converter 31.

Figure 7:
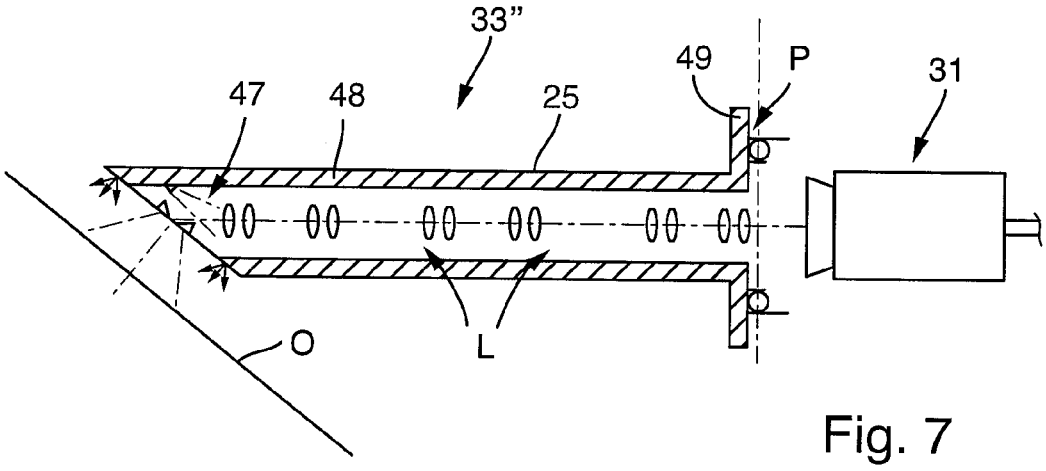
Figure 8:
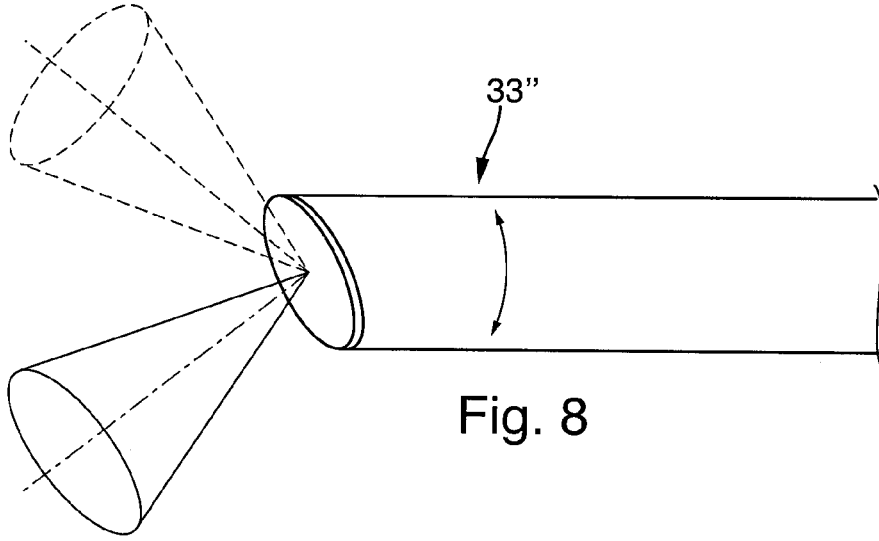

While the objective 33 of FIG. 3 is axially oriented the invention is even more useful with objectives oriented sideway as illustrated in FIGS. 6, 7 and 8. FIG. 6 illustrates an objective 33 having a mirror 46 in the vicinity of the light entry window 38 for sideward deflecting the optical axis 45. The objective 33 comprises lenses L which be placed along the length of the shaft 25 for producing a picture of an object O at the image converter 31 which may be a camera chip, a CCD camera, a CMOS camera or any other image acquiring system. The shaft 25 including the objective 33 may be turned at a plane P. This plane P may be located between the objective 33 and the image converter 31.

The same applies for the objective 33" of FIG. 7 additionally illustrated in FIG. 8 and comprising at least one light guide 48 and at least one light source 49 for illuminating the object O. The objective 33" further comprises a prism 47 at the light entry window 38 for orienting the direction of view of the laparoscopic camera sideways. Lenses L are arranged along the length of the shaft 25. Any distortion or bending of the shaft 25 will change the localization of the image of the object O at the image convertor 31. So will change the localization of the markers 39" to 42" as illustrated in FIG. 9.

Figure 9:
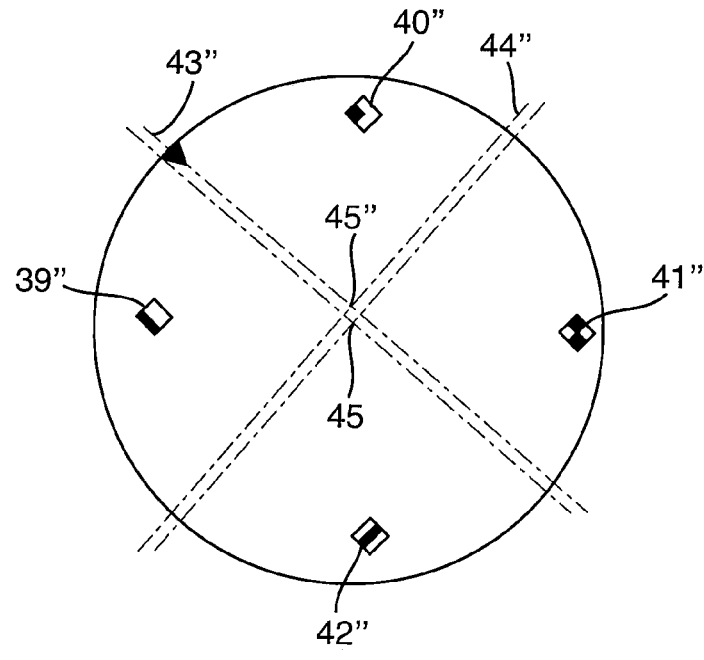

As can be taken from FIG. 9, the markers 39" to 42" will now be seen turned relative to optical axis 45 and/or shifted so that the rectangle defined by the markers 39" to 42" is turned. Additionally the symmetry lines 43" and 44" may cross a new optical axis 45" rather than original optical axis 45. The image processing unit 16 may detect these displacements and adapt or correct the mathematical camera model, which will help to register the medical image and the live image. This all can be done without providing a specific sensor for detecting rotation (or lateral displacement) of the objective.

Augmented reality applications and other applications require precise camera calibration in order to reduce the overall target registration errors. The camera calibration determines the mathematical model of the camera in order to determine how the physical world space is mapped to the camera image space and thus is highly dependent on the optics of the camera. The camera calibration algorithm normally assumes that the optics of the camera is rigidly fixed, which in fact is not at least for tilted laparoscopic cameras as illustrated in FIGS. 6 to 8. Furthermore, any mechanical play between elements of the objective and the image converter will render the optics variable. According to the invention markers 39 to 42 will be placed within the field of view of the laparoscopic camera 12, which allows for determination of rotation of the optical part and mechanical misalignment without the necessity or providing any additional sensor.

What is claimed is:

1. A laparoscopic camera arrangement comprising:
a laparoscopic camera comprising an elongated shaft extending along a center axis from a proximal end to a distal end and adapted for being introduced into an animal's or human's body;
a camera system comprising an objective with a light entry window at the distal end of the elongated shaft, the camera system comprising a camera unit with an image converter optically coupled to the objective for receiving an optical image, the objective having an optical path running through the light entry window;
at least one optical marker placed within the optical path at the distal end of the elongated shaft for being depicted on the image converter;
a position indicator rigidly connected to the elongated shaft of the laparoscopic camera, the position indicator being configured to detect a position and orientation of the elongated shaft;
a location system connected to the laparoscopic camera, the location system being configured to locate the laparoscopic camera relative to a position of the animal's or human's body; and
an image processing unit configured to detect a displacement of the at least one optical marker on the image converter due to a misalignment of the objective relative to the image converter, and to correct position data, obtained by the position indicator measuring the position and orientation of the elongated shaft, based on the displacement of the at least one optical marker detected by the image processing unit through a homography projection transformation relating the at least one optical marker to the image converter.

2. The camera arrangement according to claim 1, wherein the at least one optical marker is placed on the light entry window.

3. The camera arrangement according to claim 1, wherein the objective is rotationally fastened to the image converter.

4. The camera arrangement according to claim 1, wherein the objective with the light entry window provided thereon is rotatably mounted relative to the image converter.

5. The camera arrangement according to claim 1, wherein the light entry window is a prism.

6. The camera arrangement according to claim 1, wherein the objective comprises an axial optical axis.

7. The camera arrangement according to claim 1, wherein the objective comprises an optical axis oriented sideways.

8. The camera arrangement according to claim 1, wherein the light entry window is inclined relative to the elongated shaft.

9. The camera arrangement according to claim 1, wherein the at least one optical marker is placed in a distance from a center of the optical path in a position to be imaged on the image converter at any grade of magnification of the objective.

10. The camera arrangement according to claim 1, wherein the at least one optical marker comprises at least two, three, or four optical markers, and wherein the at least two, three, or four optical markers are placed at a periphery of the optical path.

11. The camera arrangement according to claim 10, wherein any of the at least two, three, or four optical markers comprises a unique pattern.

12. The camera arrangement according to claim 11, wherein the at least two, three, or four optical markers together form an asymmetric structure.

13. A method for correcting an image captured by a laparoscopic camera arrangement according to claim 1:

projecting the at least one optical marker placed within the optical path onto the image converter, and determining a mathematical projection model of the laparoscopic camera arrangement.

* * * * *